(12) United States Patent
Weibel et al.

(10) Patent No.: US 10,881,800 B2
(45) Date of Patent: Jan. 5, 2021

(54) DEVICE FOR DISPENSING A FLUID

(71) Applicant: SHL Medical AG, Zug (CH)

(72) Inventors: Ludwig Daniel Weibel, Waldstatt (CH); Samuel Wyler, Abtwil (CH)

(73) Assignee: SHL MEDICAL AG, Zug (CH)

( * ) Notice: Subject to any disclaimer, the term of this patent is extended or adjusted under 35 U.S.C. 154(b) by 164 days.

(21) Appl. No.: 16/305,205

(22) PCT Filed: Jun. 7, 2017

(86) PCT No.: PCT/EP2017/063749
§ 371 (c)(1),
(2) Date: Nov. 28, 2018

(87) PCT Pub. No.: WO2017/211850
PCT Pub. Date: Dec. 14, 2017

(65) Prior Publication Data
US 2019/0201624 A1     Jul. 4, 2019

(30) Foreign Application Priority Data

Jun. 8, 2016 (EP) .................................... 16173555

(51) Int. Cl.
*A61M 5/20* (2006.01)
*A61M 5/142* (2006.01)
(Continued)

(52) U.S. Cl.
CPC .......... *A61M 5/2066* (2013.01); *A61J 1/2058* (2015.05); *A61J 1/22* (2013.01); *A61M 5/1422* (2013.01); *A61M 5/16827* (2013.01)

(58) Field of Classification Search
CPC .............. A61M 5/2066; A61M 5/1422; A61M 5/16827; A61M 5/31515; A61M 5/1454;
(Continued)

(56) References Cited

U.S. PATENT DOCUMENTS

| 1,516,032 A | 11/1924 | White |
| 4,405,294 A * | 9/1983 | Albarda .................. F04B 7/045 417/488 |

(Continued)

FOREIGN PATENT DOCUMENTS

| EP | 0701061 A1 | 3/1996 |
| EP | 15152703.3 | 1/2015 |

(Continued)

OTHER PUBLICATIONS

International Search Report Corresponding to PCT/EP2017/063749 dated Sep. 14, 2017.

(Continued)

*Primary Examiner* — Jason E Flick
*Assistant Examiner* — Tasnim Mehjabin Ahmed
(74) *Attorney, Agent, or Firm* — McDonnell Boehnen Hulbert & Berghoff LLP

(57) ABSTRACT

A device (1) and the use thereof for dispensing fluid under aseptic conditions. The device (1) comprises conveying device (2) and container (3) with a variable inner volume. The conveying device comprises cylinder (4) with at least three openings (5, 6, 7) which are arranged along longitudinal central axis (11). Displaceable first and second pistons (9, 10) are arranged in the cylinder. The end faces (11, 12) of the pistons and inner wall (13) of the cylinder, delimit a variable fluid volume (14). The first opening is brought into fluidic communication with dispensing opening (15) and the second opening is brought into fluidic communication with the container. Each of the pistons comprise three seals (16, 16', 16") which are offset and sealingly close off the cylinder. Adjacent piston seals have inner spacing (di) which is equal to a shortest spacing (aA1) between two adjacent openings (5, 6 or 6, 7).

15 Claims, 10 Drawing Sheets

Figure 1:
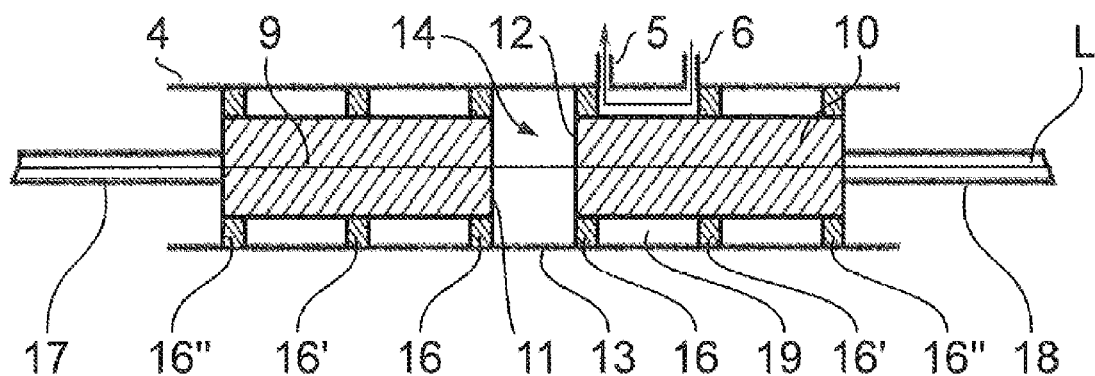

(51) Int. Cl.
*A61M 5/168* (2006.01)
*A61J 1/22* (2006.01)
*A61J 1/20* (2006.01)

(58) Field of Classification Search
CPC ........ A61M 5/1408; A61J 1/2058; A61J 1/22; A61J 1/2096; F04B 7/045; F04B 13/00
See application file for complete search history.

(56) References Cited

U.S. PATENT DOCUMENTS

| | | |
|---|---|---|
| 5,513,779 A | 5/1996 | Reich |
| 5,639,220 A | 6/1997 | Hayakawa |
| 7,726,955 B2 | 6/2010 | Ryser et al. |
| 8,758,323 B2* | 6/2014 | Michaud ............... F04B 43/113 604/500 |
| 2003/0028145 A1 | 2/2003 | Duchon et al. |
| 2005/0177111 A1 | 8/2005 | Ozeri et al. |
| 2008/0118376 A1* | 5/2008 | Verrilli ................. F04B 3/00 417/383 |
| 2011/0073620 A1 | 3/2011 | Verrilli |
| 2011/0196337 A1 | 8/2011 | Brandt et al. |
| 2015/0290389 A1* | 10/2015 | Nessel ................. F04B 3/00 604/500 |
| 2016/0213851 A1 | 7/2016 | Weibel et al. |

FOREIGN PATENT DOCUMENTS

| | | |
|---|---|---|
| EP | 2 992 916 A1 | 3/2016 |
| EP | 3 050 585 A1 | 8/2016 |
| GB | 1508665 | 4/1978 |
| WO | 2005039674 A1 | 5/2005 |
| WO | 2014090745 A1 | 6/2014 |
| WO | 2014207532 A1 | 12/2014 |

OTHER PUBLICATIONS

Written Opinion Corresponding to PCT/EP2017/063749 dated Sep. 14, 2017.

* cited by examiner

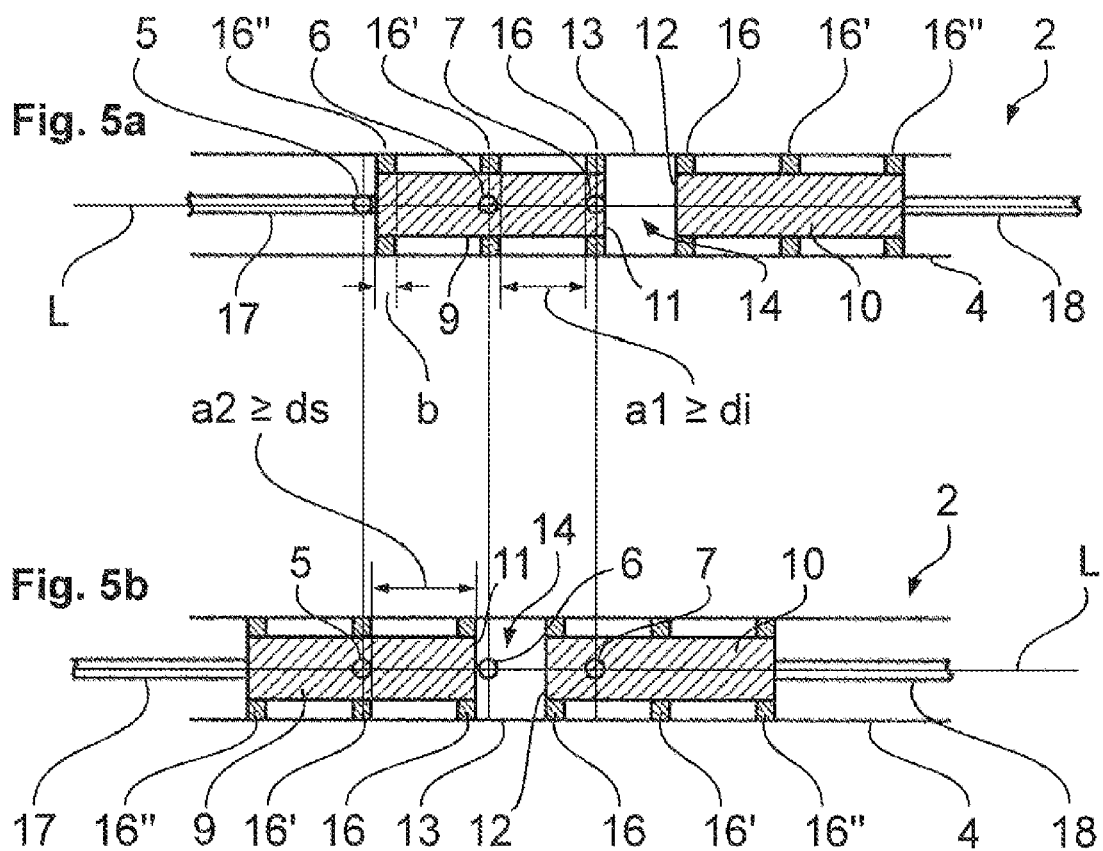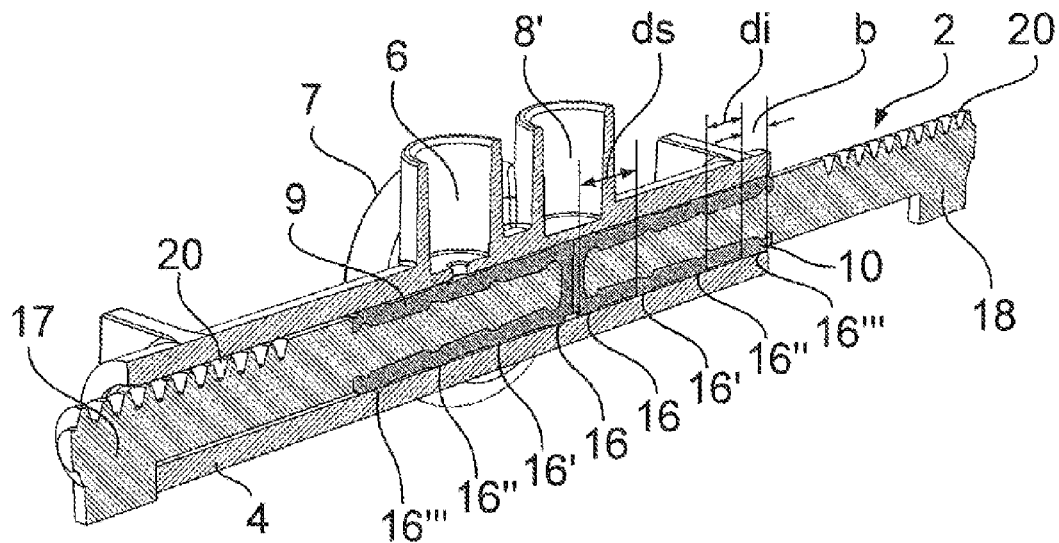
Fig. 6

DEVICE FOR DISPENSING A FLUID

The present invention relates to a device and the use thereof for dispensing a fluid, in particular under aseptic conditions, according to the preambles of the independent claims.

During the administration of fluid formulations of active pharmaceutical substances, it is in most cases necessary to dispense well-defined volumes to a patient. Often, medicaments have to be dispensed via an injection for this purpose. For parenteral administration, syringes, medicament pens (so-called pens) or medicament pumps are used in this case.

In particular with preparations which have to be administered over a relatively long period of time and/or or in accordance with a precisely predetermined program, syringes and pens are increasingly being replaced by medicament pumps. A main application field is in this instance the administration of insulin to patients suffering from diabetes. Diabetics have, several times a day under often significantly changing conditions, to administer themselves an insulin dose by means of subcutaneous injection. The use of a medicament pump is a significant improvement of their quality of life since the dispensing via it can be automated to the greatest possible extent. In addition to improved comfort for the patient, improved hygiene and consequently a higher level of patient safety can also be achieved as a result of the use of such a pump. Insulin preparations are particularly suitable for this purpose since they are provided by most manufacturers as a ready-to-inject solution in a cartridge.

Medicament pumps which are suitable for being fitted to the body of a patient in order to administer a preparation continuously over a relatively long period of time generally comprise a container and a conveying device which conveys the fluid from the container to a connection or to an injection system. However, the container and the conveying device may also be combined in one component, for example, in the form of an injection pump. An injection system may, for example, be suitable for placing an indwelling cannula which remains in the body of a patient for the entire administration period.

Such medicament pumps are generally only suitable for administering ready-to-inject solutions. They therefore have with respect to the type of medicament which is intended to be administered a comparatively low level of flexibility.

The European Patent Application with the file reference EP 15152703.3 discloses a metering device which comprises a conveying device which is driven by at least one conveying drive for conveying a fluid from the inner space of a container. The fluid can be conveyed by means of the conveying device from the container to a dispensing opening. The conveying device comprises a cylinder having at least one intake opening and at least one discharge opening in a cylinder inner wall, and a first piston and a second piston. The first piston and the second piston are supported displaceably in the longitudinal direction inside the cylinder. Furthermore, the first piston and the second piston delimit between the end sides thereof together with a portion of the cylinder inner wall a variable fluid volume. By using such a conveying device having a cylinder and two pistons, other functions can be performed using the metering device described in addition to the pure conveying function. The cylinder can thus in addition to the intake opening and the outlet opening also have other openings which are also arranged to be offset therein. Consequently, for example, it is possible to connect an analysis device for analyzing a conveyed fluid to the conveying device. However, it is also possible to connect several containers via different openings to the conveying device, whereby a mixing of substances, for example in order to reconstitute a lyophilisate, can be achieved.

As described in the application mentioned, the pistons which are arranged in the cylinder may comprise one or more seals in order to close the transition from the pistons to the cylinder inner wall in a sealed manner. The use of seals has the advantage that a high sealing action can be achieved even with comparatively low production tolerances of the cylinder and piston.

However, it has been found that such a metering device with seals on the pistons in applications in which more than two openings which are arranged offset on the cylinder are involved, has considerable disadvantages. Thus, it may, for example, be the case that two or more openings in the cylinder are brought directly into fluid communication with each other by means of an intermediate space between two seals on a piston. It is thereby possible for an overflow of a fluid from one opening to an adjacent one to occur. However, in embodiments of the metering device in which an overflow of a fluid from one opening in the cylinder to an adjacent one is prevented as a result of the spacing of the sealing elements on the pistons, indirect overflowing may also occur. This may occur as a result of the fact that air or other gases which are located in an intermediate space between two seals are compressible, whereby a fluid which is under pressure can be introduced into the intermediate space. If a connection to an opening is then interrupted and one is produced with respect to an adjacent opening, the compressed substance mixture can expand in the intermediate space and be discharged from the adjacent opening. These problems are a clear impairment of the functionality of such metering devices.

An object of the present invention is therefore to overcome the disadvantages in the prior art.

In particular, an object of the present invention is to provide a device which can be used in a versatile manner and which is structurally simple for dispensing a fluid of the above-mentioned type, in which a direct or indirect overflow between the openings in the cylinder of the conveying device is prevented. In this instance, the conveying device is intended to be reliable in terms of operation and suitable for producing comparatively high fluid pressures.

These objectives are achieved by a device which has the features in claim 1.

The device for dispensing a fluid, in particular under aseptic conditions, comprises a conveying device and a container having a variable inner volume. The conveying device comprises a cylinder having at least three openings which are arranged in series along a longitudinal center axis and via which the fluid can be conveyed. Furthermore, the conveying device comprises a first and a second piston, wherein the first and the second piston are arranged in the cylinder so as to be able to be displaced along the longitudinal center axis. The first piston and the second piston delimit between the end sides thereof together with a portion of the cylinder inner wall a variable fluid volume. The first opening can be brought into fluid communication with a dispensing opening of the device and the second opening can be brought into fluid communication with the container. The first piston and the second piston each comprise at least three seals which are arranged to be offset in the longitudinal direction and which close the cylinder in a sealing manner. Adjacent seals on a piston have in this instance an inner spacing which is at a maximum the same size as the shortest spacing between two adjacent openings.

A container with a variable inner volume is intended in this context to be understood to be a container having an inner space in which at least one wall portion can be moved. Consequently, the inner volume of the container can be adapted to the volume of the fluid which is contained therein. This is particularly advantageous when the fluid is in the form of a liquid. On the one hand, a ventilation of the container can thus be dispensed with. On the other hand, the container, when it is not completely filled with a liquid, does not contain any gas, in particular no air. A conveying of the liquid from the container by means of the conveying device regardless of the orientation of the device with respect to gravitational force is thereby enabled without there being any risk of air or other gas being drawn in by the conveying device. A container with a variable inner volume may, for example, be a syringe or cartridge having a pulled piston or a liquid bag (a so-called bag).

As a result of the described spacing of adjacent seals on the pistons in relation to the shortest spacing between two adjacent openings in the cylinder, a direct overflow of a fluid from one opening to the other via an intermediate space between the seals can be prevented. The described device can in this instance be used in a versatile manner for a variety of applications which extend beyond the simple conveying of a fluid, such as, for example, the additional analysis of a fluid with an analysis device or the reconstitution of a lyophilisate.

In a simple embodiment, the conveying device comprises a cylinder having precisely three openings which are arranged in series along the longitudinal center axis thereof, and in each case precisely three seals on the two pistons.

The seals on the pistons can be spaced apart in a uniform manner. This enables a good sealing action and an advantageous sliding behavior of the pistons within the cylinder to be achieved.

The spacing between the first opening and the second opening may be at least the same size as the lateral spacing between two adjacent seals of the pistons. Consequently, an indirect overflow of a fluid from the second opening to the first can be prevented. This is required in particular when a fluid is intended to be conveyed to the second opening and in this instance at the second opening a positive pressure builds up. This is, for example, the case with a resilient bag which is connected to the second opening.

The seals may have a width which is at least equal to the longitudinal extent, in particular the diameter, of the openings in the cylinder. Consequently, it is possible to prevent a fluid from being able to overflow via an individual opening from one side of a seal to the other.

The first piston and the second piston may each comprise at least the same number of seals, which are arranged to be offset in a longitudinal direction, as the cylinder has openings. With this minimal number of seals, it can be ensured that an intermediate space which is closed between two seals is always available for each individual opening in the cylinder, which prevents a fluid from flowing out or overflowing.

The conveying device may comprise a cylinder having four openings which are arranged in series along the longitudinal center axis thereof and via which the fluid can be conveyed. The third opening may be able to be brought into fluid communication with a container, in particular a phial, containing a lyophilisate and the fourth opening may be able to be brought into fluid communication with a container, in particular a phial, containing a solvent. Consequently, there is provided a device which in particular enables the reconstitution of the lyophilisate under aseptic conditions in a manner which is simple and reliable for the user.

The conveying device may be able to be driven by at least one conveying drive, preferably the first piston by a first conveying drive and the second piston by a second conveying drive. In particular as a result of the use of two independent conveying drives, the flexibility of the device with respect to the use thereof is further increased.

The device may comprise an injection device for preferably continuous subcutaneous dispensing of a fluid to a patient. The use of an injection device enables the subcutaneous dispensing of the fluid to a patient to be automated to the greatest possible extent. The patient can thereby use the said device irrespective of the presence of medical staff with a high degree of comfort and safety.

The device may comprise a drive module and a dispensing module which are constructed so as to be able to be connected and/or separated from each other by a user. The drive module may optionally comprise at least portions of a conveying drive, in particular a rotary drive, and/or optionally a fitting drive of an injection device. Furthermore, the drive module may also comprise a battery for supplying the drives and a control unit for controlling the device, in particular the drives. There may also be provided in the drive module communication means via which an external operating unit can be connected to the control unit. The dispensing module may comprise at least the container and the conveying device and, where applicable, the injection device.

The drive module and the dispensing module may be constructed in such a manner that the drives can be readily coupled by means of corresponding coupling means directly or indirectly to the conveying device and/or the injection device. To this end, for example, positive-locking and/or non-positive-locking plug type couplings can be used. For simple replacement, the two modules may, for example, be able to be coupled to each other and/or separated from each other by means of a snap-fit coupling.

This has the advantage that the drive module which contains no hygienically relevant components has to be neither sterilized nor assembled in a clean room before its first use. Consequently, the production and purchase costs of the device can be reduced. In addition, the drive module can be readily reused which also lowers the operating costs of the device. Furthermore, this embodiment provides more flexibility in the case of structural modifications. Although the dispensing module which contains all hygienically relevant components has to be sterilized, since it does not contain any extremely complex components it can be produced at a lower cost and disposed of after a single use. Since the drive module and the dispensing module are constructed so as to be able to be connected to and separated from each other, the use of the dispensing device by a user nonetheless remains extremely simple. As a result, with consistent user-friendliness and patient safety, the costs of procuring and operating the device can be lowered.

The present invention further relates to the use of a device described above for dispensing a fluid, in particular under aseptic conditions.

Figure 2:
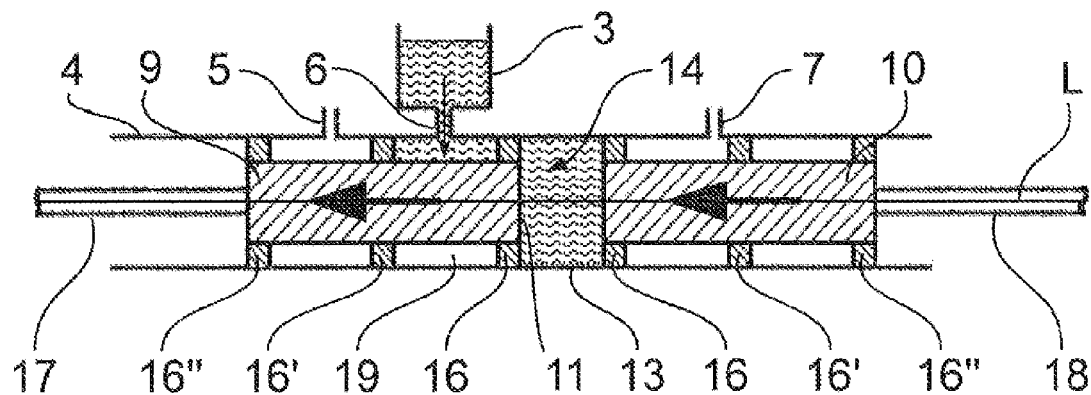
Figure 3:
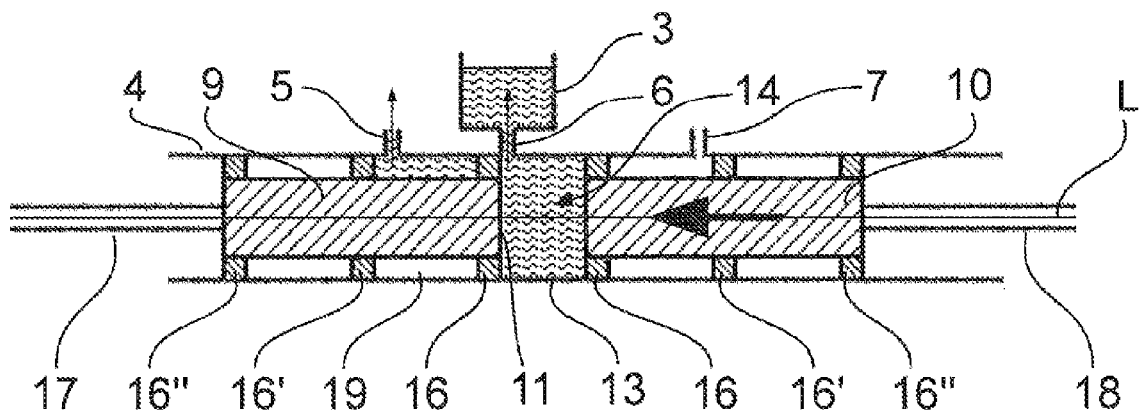
Figure 4:
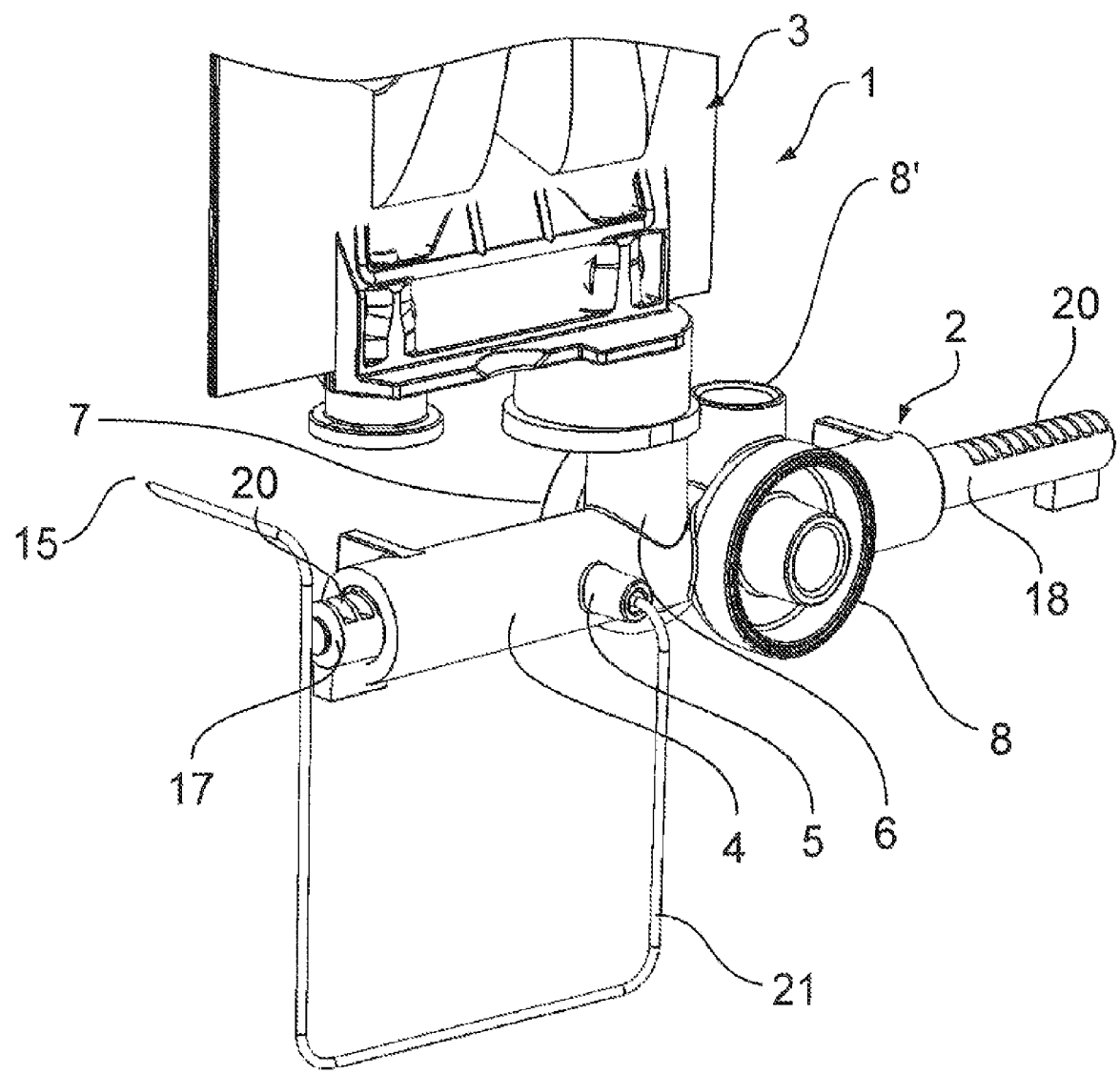
Figure 7:
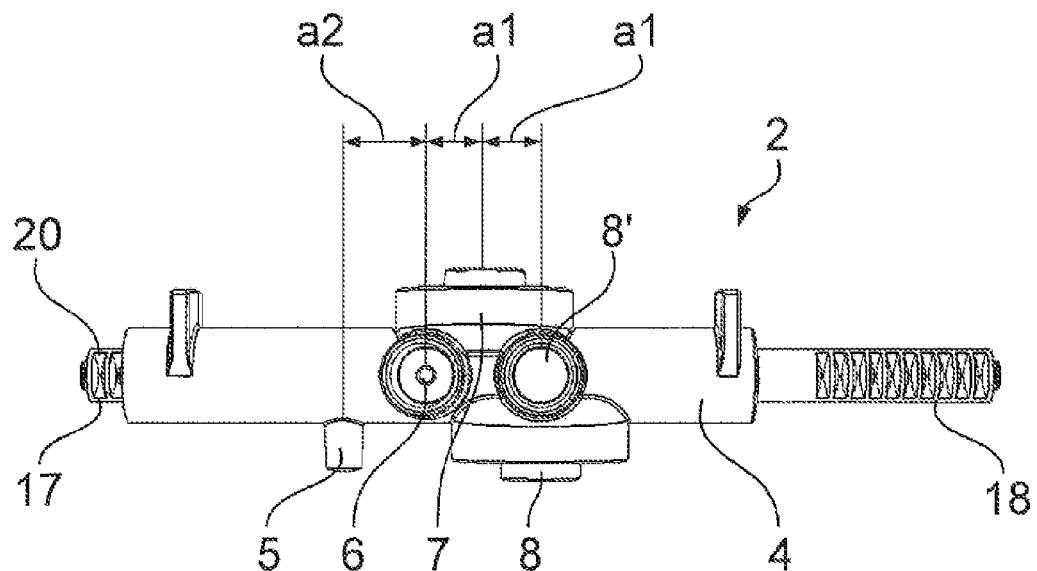
Figure 8:
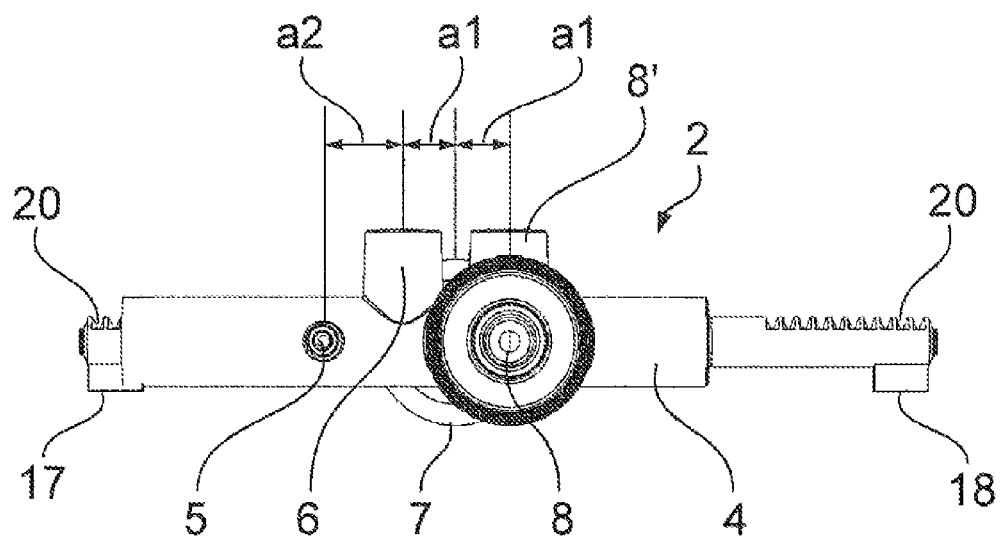

Other advantages and individual features of the invention will be appreciated from the following description of an embodiment and from the drawings:

In the schematic drawings:

FIG. 1: shows a conveying device from the prior art;

FIGS. 2 and 3: show another example of a conveying device from the prior art;

FIG. 4: is a perspective illustration of a device according to the invention;

FIGS. 5a and 5b: are simplified illustrations of a conveying device of a device according to the invention;

FIG. 6: is a perspective sectioned view of a device according to the invention according to FIG. 4;

FIG. 7: is a plan view of the conveying device according to FIGS. 4 and 6;

FIG. 8: is a side view of the conveying device according to FIGS. 4, 6, and 7;

FIGS. 9 to 14: are perspective illustrations of a sequence of steps which illustrates the reconstitution of a lyophilisate with a device according to the invention.

FIG. 1 illustrates a conveying device from the prior art. The said conveying device comprises a cylinder 4 in which the pistons 9, 10 are supported so as to be able to be displaced in the longitudinal direction. The pistons 9, 10 enclose with the end sides 11, 12 thereof and with a cylinder inner wall 13 a variable fluid volume 14. The pistons 9, 10 each have three seals 16, 16', 16" which close the transition to the cylinder inner wall 13 in a sealing manner. The pistons 9, 10 are driven by means of the piston rods 17, 18. In the piston 4, two openings 5, 6 which are arranged to be offset along the longitudinal axis 11 are arranged. It can be seen that the seals 16, 16' are spaced apart in the pistons 9, 10 in such a manner that, depending on the position of the intermediate space 19 which is closed between the seals 16 and 16', a direct connection between the openings 5 and 6 is produced. As a result, as shown in the present illustration, an uncontrolled direct overflow of a fluid, for example, from the opening 6 to the opening 5 may occur.

FIGS. 2 and 3 relate to another disadvantageous aspect of a conveying device from the prior art. The said device is configured in such a manner that a fluid from the opening 7 which is arranged in the cylinder 4 in a first step can be conveyed via the opening 6 to the container 3. In a second step, a conveying of the fluid from the container 3 to the opening 5 is provided. When the container 3 is filled with a fluid, at the opening 6 a fluid pressure, for example, a hydrostatic pressure, is built up. In FIG. 2, the said device is shown with simultaneous displacement of the pistons 9, 10 in the same direction from the opening 7 to the opening 6. It can be seen that, in this procedure, the opening 6 is in fluid communication with the intermediate space 19 enclosed between the seals 16 and 16'. The intermediate space 19 is filled with a gas, generally with air. Since the gas is compressible and there is a fluid pressure applied at the opening 6, there is a compression of the gas and an introduction of the fluid into the intermediate space 19. FIG. 3 shows the discharge of the fluid from the intermediate space 14 into the container 3. The piston 9 is in this instance retained in a stationary manner, whilst the piston 10 is moved toward it in order to reduce the volume 14 which is enclosed between the pistons 9, 10. It can be seen that the volume 19 which is enclosed between the seals 16, 16' is now in fluid communication with the opening 5. Since from the step shown in FIG. 2 a compressed fluid mixture is still located in the volume 19, there is an uncontrolled discharge from the opening 5. On the whole, there accordingly results an uncontrolled indirect overflow of fluid from the opening 6 to the opening 5.

FIG. 4 shows a device 1 according to the invention. The said device 1 comprises a conveying device 2 and a container 3 which in this instance is constructed as a collapsible bag. The conveying device 2 is composed of a cylinder 4 in which the two pistons 9, 10 are supported so as to be able to be displaced in a longitudinal direction. The pistons 9, 10 cannot be seen in the present illustration. However, the piston rods 17 and 18 which are connected thereto can be seen. In the embodiment shown, the cylinder 4 has a total of four openings 5, 6, 7, 8 which are arranged to be offset in the longitudinal direction. The opening 8' is in this instance a blind opening in which the wall of the cylinder 4 is not pierced. Depending on the embodiment of the conveying device 2, there may be an aperture in the opening 8 and/or in the opening 8'. The opening 5 is connected in fluid terms via the cannula 21 to the discharge opening 15. The opening 6 is in fluid communication with the container 3. The openings 7 and 8 can also be brought into fluid communication with containers, in particular with phials.

FIGS. 5a and 5b show a simplified illustration of a conveying device 2 for a device 1 according to the invention. In FIG. 5a, the inner spacing di between the seals 16 and 16' or 16' and 16" is selected in such a manner that this is at a maximum equal to the spacing a1 between the second opening 6 and the third opening 7. A direct fluid connection between the opening 6 and the opening 7 may consequently not be produced, which impedes unintentional overflow of a fluid. As can be seen in FIG. 5b, the spacing a2 between the first opening 5 and the second opening 6 is selected in such a manner that it is greater than or equal to the lateral spacing ds between the seals 16 and 16'. Consequently, an unintentional indirect overflow of a fluid from the opening 6 to the opening 5 can be prevented, even if there is a fluid pressure applied at the opening 6. The conveying device 2 shown in FIGS. 5a and 5b is consequently suitable in a first step for conveying a fluid from the third opening 7 to the second opening 6. In a second step, the fluid can be conveyed from the second opening 6 to the first opening 5. In a device 1 according to the invention, the first opening 5 can be brought into fluid communication with a dispensing opening of the device 1 whilst the second opening 6 can be brought into fluid communication with a container.

FIG. 6 shows a plurality of details of a conveying device 2 according to FIG. 4. The cylinder 4 comprises a total of four openings 5, 6, 7 and 8, of which in this instance only the openings 6 and 7 can be seen. The opening 8' is constructed as a blind opening. The two pistons 9 and 10 comprise a resilient material and are inserted onto the piston rods 17 and 18. On each piston, four seals 16, 16', 16" and 16''' are constructed integrally. In the illustration described, both the inner spacing dl between two seals and the lateral spacing da are illustrated. In addition, it can be seen that a single seal 16, 16', 16''' and 16" has a width b.

FIG. 7 is a plan view of the conveying device 2 of a device 1 according to the invention according to FIGS. 4 and 6. From this perspective, all four openings 5, 6, 7 and 8 can be seen. In addition, it can clearly be seen that the opening 8' is constructed as a blind opening. The spacing a1 between the second opening 6 and the third opening 7 is equal to the spacing between the third opening 7 and the fourth opening 8. The spacing a2 between the first opening 5 and the second opening 6 is greater than the spacing a1. FIG. 8 shows the conveying device 2 according to FIG. 7 alternatively as a side view. It is particularly possible in this instance to clearly see on the piston rods 17 and 18 the tooth profiles 20 via which a conveying drive which is not described in greater detail in this instance can act on the piston rods 17 and 18.

Figure 9:
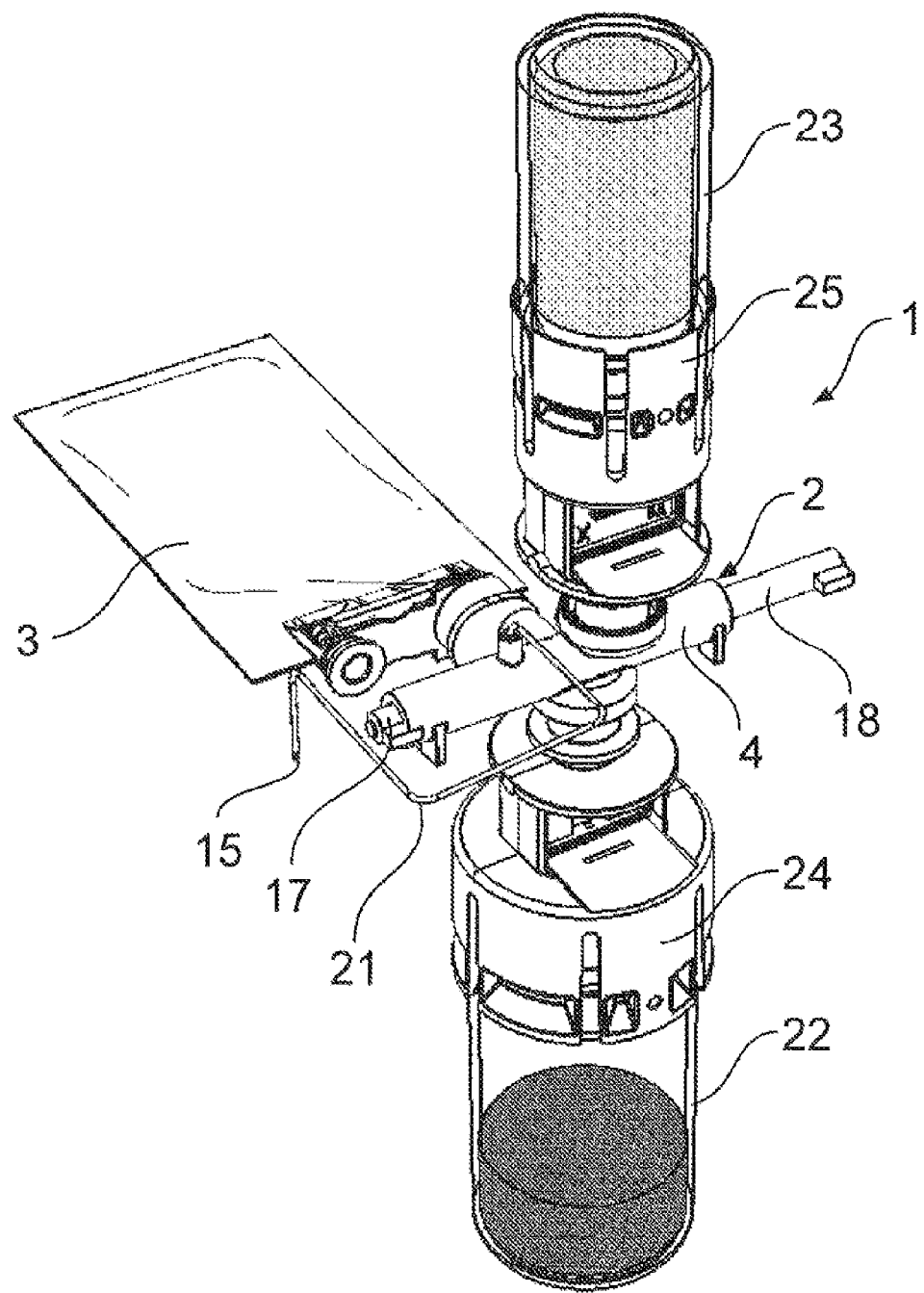
Figure 10:
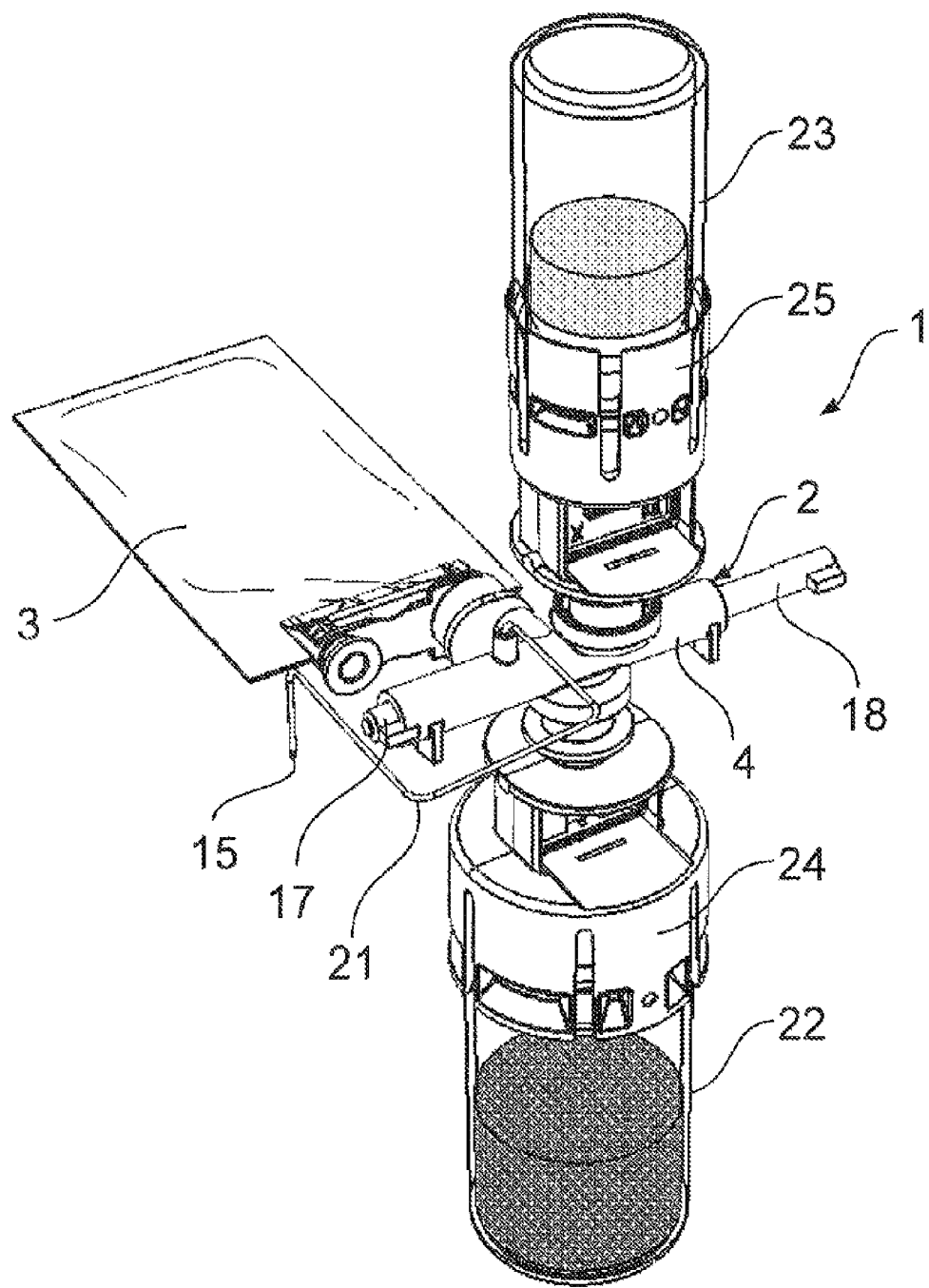
Figure 11:
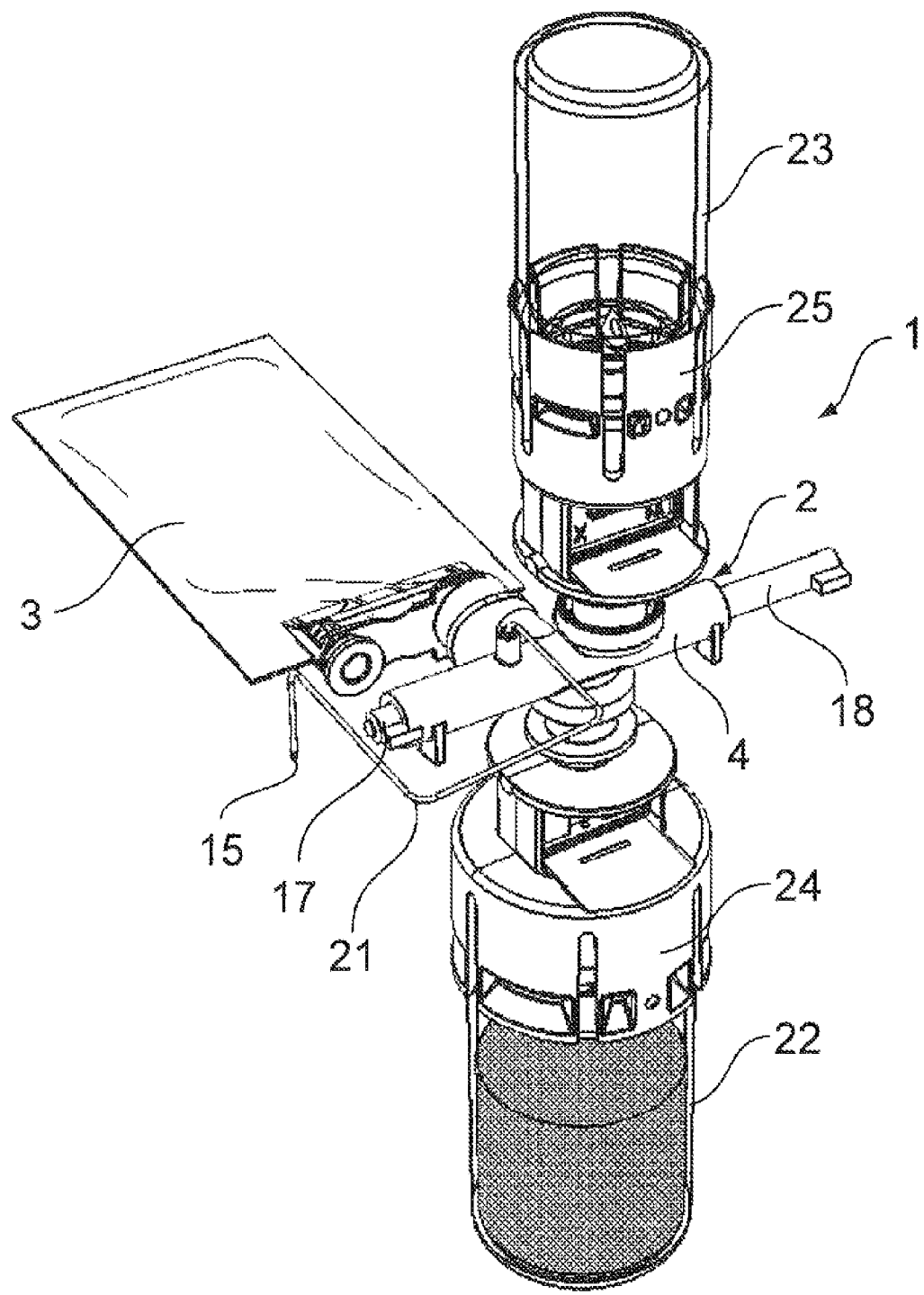
Figure 12:
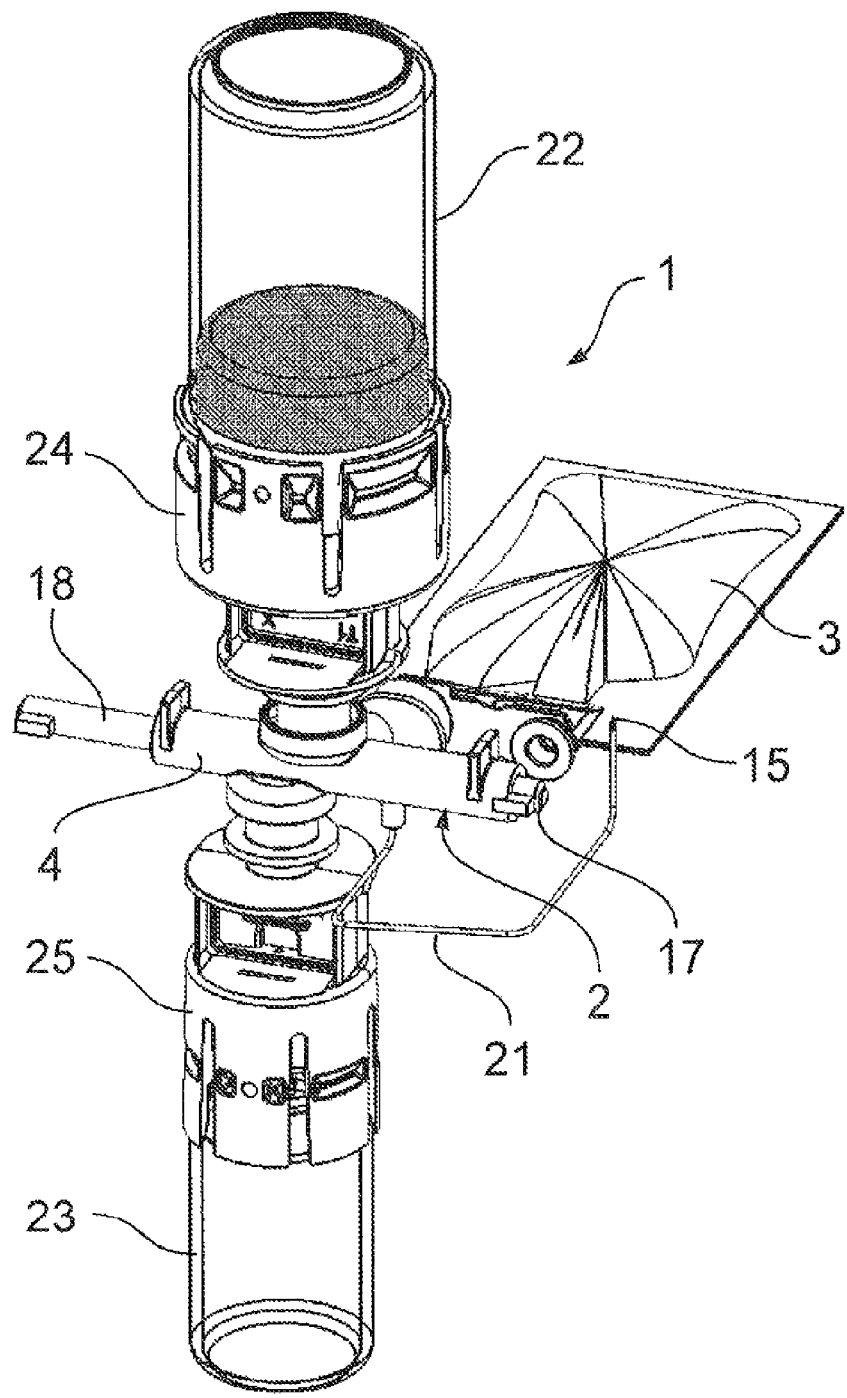
Figure 13:
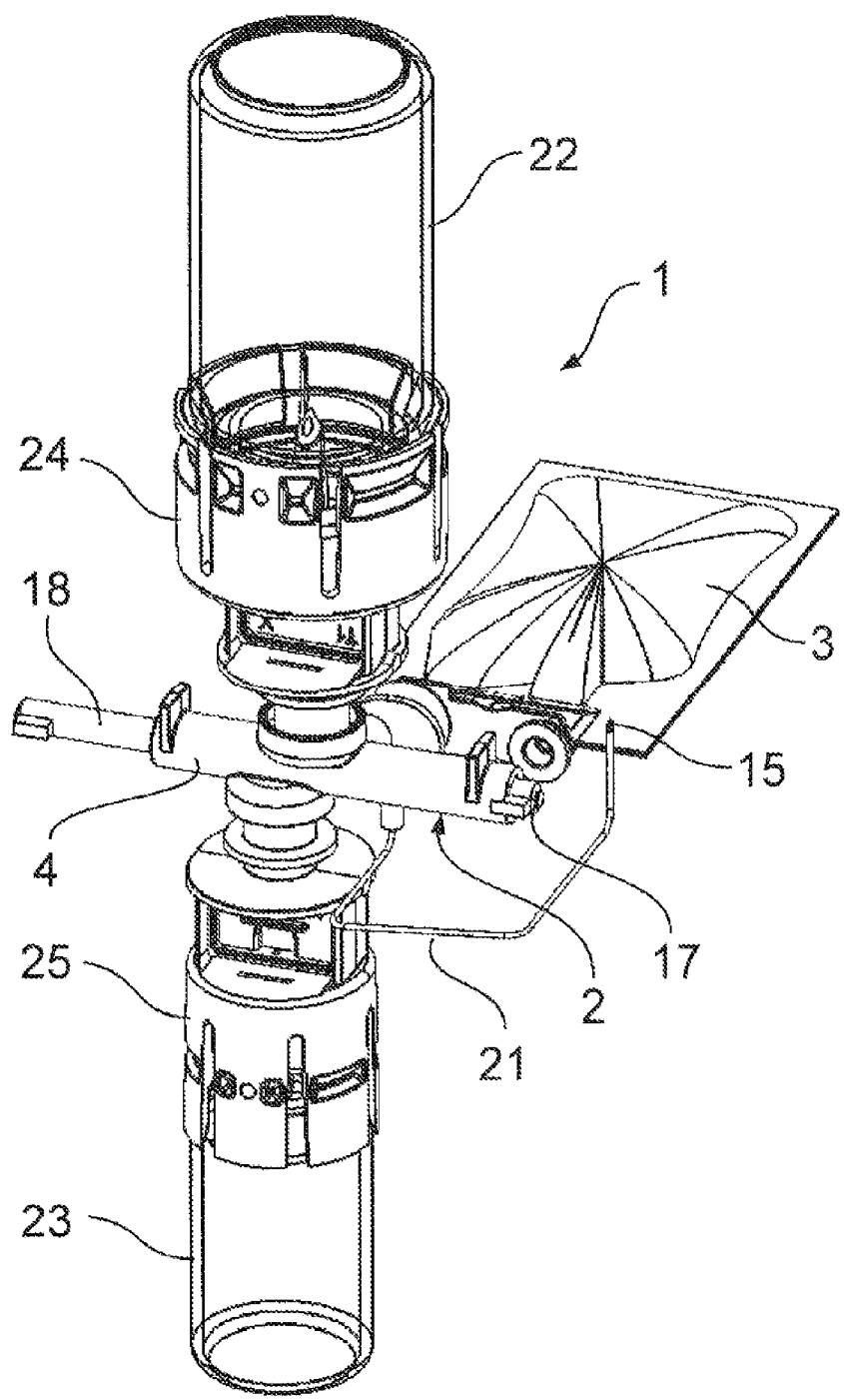
Figure 14:
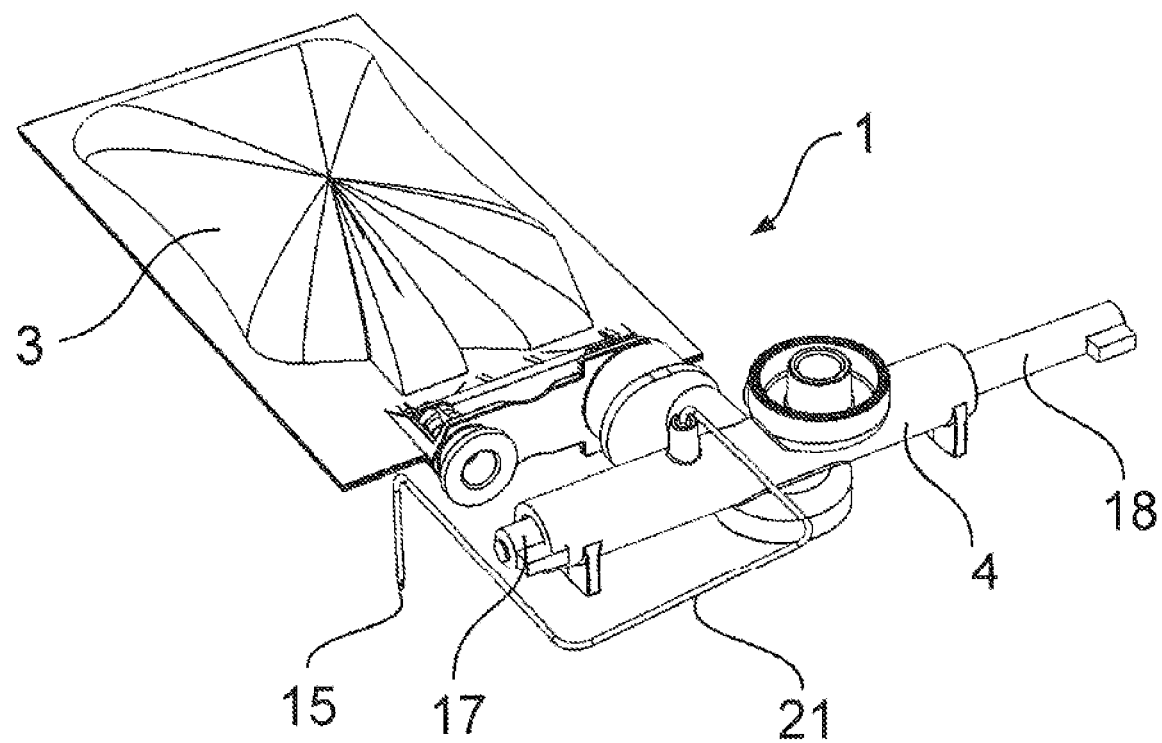

FIG. 9 shows a device 1 according to the invention according to FIGS. 4, 6, 7 and 8 to which a first container 22 having a lyophilisate and a second container 23 having a solvent are connected by means of coupling elements 24 and 25. In the illustration according to FIG. 10, the solvent present in the container 24 is conveyed with the conveying device 2 from the opening 8 to the opening 7 in order to dissolve the lyophilisate which is present in the container 22. In FIG. 11, this procedure is terminated. All the solvent has been conveyed from the container 23 into the container 22, where the lyophilisate has completely dissolved. In FIG. 12, the solution contained in the container 22 is conveyed by the conveying device 2 from the opening 7 to the opening 6 and consequently to the container 2. To this end, the device 1 is rotated through 180° so that the solution present in the container 22 can be completely drawn in by the conveying device 2. In FIG. 13, the transfer of the solution from the container 22 to the container 3 which in this instance is constructed as a collapsible bag is terminated. It can be seen that the container 3 is clearly distended. The containers 22 and 23 and the coupling elements 24 and 25 can now be removed from the device 1, as shown in FIG. 14. The handling of the device 1 for actual dispensing of the solution, for example, to a patient, is now substantially simplified since the device 1 is less bulky. During the actual dispensing, there is produced a transfer of the solution from the container 3 via the opening 6 to the opening 5 and consequently further via the cannula 21 to the dispensing opening 15.

The invention claimed is:

1. A device for dispensing a fluid comprising:
   a conveying device, and
   a container having a variable inner volume,
   wherein the conveying device comprises a cylinder having at least three openings which are arranged in series along a longitudinal center axis and via which the fluid can be conveyed,
   a first piston,
   a second piston,
   the first and the second piston are arranged in the cylinder so as to be able to be displaced along the longitudinal center axis and between end sides of the first and the second piston together with a portion of the cylinder inner wall delimit a variable fluid volume,
   a first opening of the at least three openings can be brought into fluid communication with a dispensing opening of the device and a second opening of the at least three openings can be brought into fluid communication with the container,
   the first and the second piston each comprise at least three seals which are arranged to be offset, in the longitudinal direction, and which close the cylinder in a sealing manner, and
   adjacent seals of the at least three seals on each piston have an inner spacing which is at a maximum a same size as a shortest spacing between two adjacent openings of the at least three openings.

2. The device according to claim 1, wherein the seals on the pistons are spaced apart in a uniform manner.

3. The device according to claim 1, wherein the spacing between the first opening and the second opening is at least the same size as a lateral spacing between two adjacent seals on the pistons.

4. The device according to claim 1, wherein the seals have a width which is at least equal to a longitudinal extent of the openings.

5. The device according to claim 1, wherein the first piston and the second piston each comprise at least the same number of seals which are arranged to be offset, in a longitudinal direction, as the cylinder has openings.

6. The device according to claim 1, wherein the conveying device comprises a cylinder having four openings which are arranged in series along the longitudinal center axis thereof and via which the fluid can be conveyed, and the third opening can be brought into fluid communication with a container containing a lyophilisate and the fourth opening can be brought into fluid communication with a container containing a solvent.

7. The device according to claim 1, wherein the conveying device is driven by at least one conveying drive.

8. The device according to claim 1, further comprising an injection device for subcutaneous dispensing of a fluid to a patient.

9. The device according to claim 1, further comprising a drive module and a dispensing module which are constructed so as to be able to be at least one of connected to or separated from each other by a user, and the dispensing module comprises at least the container and the conveying device and an injection device.

10. The device according to claim 9, wherein the drive module comprises at least one module selected from the group of at least portions of the conveying drive and a fitting drive of the injection device.

11. The device according to claim 1, wherein the dispensing of the fluid occurs under aseptic conditions.

12. The device according to claim 1, wherein the seals have a width which is at least equal to a diameter of the openings.

13. The device according to claim 1, wherein the first piston is driven by a first conveying drive and the second piston is driven by a second conveying drive.

14. The device according to claim 1, further comprising an injection device for subcutaneous dispensing of a fluid to a patient, and the subcutaneous dispensing is continuous.

15. The device according to claim 14, wherein the drive module comprises at least a rotary drive.

* * * * *